United States Patent [19]

Köpf-Maier et al.

[11] Patent Number: 4,851,430
[45] Date of Patent: Jul. 25, 1989

[54] COMPOSITIONS CONTAINING METALLICENIUM SALTS AND UTILIZATION THEREOF AS CYTOSTATIC AGENTS FOR COMBATTING TUMORS SUSCEPTIBLE THERETO

[76] Inventors: Petra Köpf-Maier; Hartmut Köpf, both of Bundesring 33, 1000 Berlin 42, Fed. Rep. of Germany; Eberhard W. Neuse, 5 Neeron Road, Blairgowrie-Randburg 2194, South Africa

[21] Appl. No.: 784,291

[22] PCT Filed: Feb. 8, 1985

[86] PCT No.: PCT/EP85/00047
 § 371 Date: Oct. 3, 1985
 § 102(e) Date: Oct. 3, 1985

[87] PCT Pub. No.: WO85/03507
 PCT Pub. Date: Aug. 15, 1985

[30] Foreign Application Priority Data

Feb. 8, 1984 [DE] Fed. Rep. of Germany ....... 3404443

[51] Int. Cl.$^4$ .............................. A61K 31/295
[52] U.S. Cl. ..................... 514/502; 514/63; 514/501; 514/492; 514/503; 514/505
[58] Field of Search ............... 514/501, 502, 492, 503, 514/505, 63

[56] References Cited

U.S. PATENT DOCUMENTS 4,608,387 8/1986 Kopf et al. ................. 514/492

OTHER PUBLICATIONS

Castagnola et al., J. of Organometallic Chem., vol. 60, pp. C17, 18 (1973).
Nesmeyanov et al., Chem. Ber., vol. 93, p. 2729 (1960).
Akaroni et al., J. of Organomettalic Chem., vol. 22, p. 179 (1970).
Aly et al., Chem. Commun., p. 404 (1965).

Primary Examiner—Mary C. Lee
Assistant Examiner—Bernard I. Dentz
Attorney, Agent, or Firm—Birch, Stewart, Kolasch & Birch

[57] ABSTRACT

Metallicenium salts of the general formula I

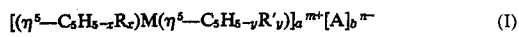
$$[(\eta^5-C_5H_{5-x}R_x)M(\eta^5-C_5H_{5-y}R'_y)]_a{}^{m+}[A]_b{}^{n-} \qquad (I)$$

in which M is Fe, Co, Ni, Ru or Os; $C_5H_{5-x}R_x$ and $C_5H_{5-y}R'_y$ denote cyclopendadienyl rings which, independently of one another, can be unsubstituted (x and y=0) or mono-, di-, tri-, tetra- or penta-substituted (x and y=1, 2, 3, 4 or 5), and in which R and R' independently of one another represent identical or different substituents and denote alkyl, cycloalkyl, hydroxyalkyl, aminoalkyl, halogenoalkyl, alkenyl, aryl, aralkyl, ferrocenyl, ferrocenylium, ferrocenylalkyl, acyl, halogenyl, trialkylsilyl, tricycloalkylsilyl, triarylsilyl, triaralkylsilyl or carboxyl, ester, amide or hydrazide groups, or R and R' together form an alkylene bridge with 2 to 4 bridge atoms; a, b, m and n are integers, and m has the value 1 or 2, n has the value 1, 2 or 3 and $a \times m = b \times n$; and A is a complexating or very bulky anion which stabilizes the metallicenium cation; and solvates of these salts, for use as medicaments, in paticular as cytostatics in combating tumors susceptible thereto.

14 Claims, No Drawings

COMPOSITIONS CONTAINING METALLICENIUM SALTS AND UTILIZATION THEREOF AS CYTOSTATIC AGENTS FOR COMBATTING TUMORS SUSCEPTIBLE THERETO

Metallicenium compounds are formed by chemical or electrochemical one-electron oxidation of metallocenes; see Wilkinson et al., J. Am. Chem. Soc., Volume 74, page 2125 (1952) and Rosenblum, "Chemistry of the Iron Group Metallocenes", Wiley, N.Y. (1965). They are salt-like substances, some of which are hydrophilic or even water-soluble. In these compounds, the cyclopentadienyl ring is linked to the central metal atom by a hapto-5-bond.

It has now been found that metallicenium compounds have a chemotherapeutic action, and in particular display cytostatic properties.

The invention relates to metallicenium salts of the general formula I

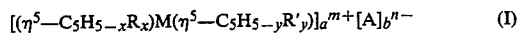

$$[(\eta^5-C_5H_{5-x}R_x)M(\eta^5-C_5H_{5-y}R'_y)]_a{}^{m+}[A]_b{}^{n-} \qquad (I)$$

in which M is Fe, Co, Ni, Ru or Os; $C_5H_{5-x}R_x$ and $C_5H_{5-y}R'_y$ denote cyclopendadienyl rings which, independently of one another, can be unsubstituted (x and y=0) or mono-, di-, tri-, tetra- or penta-substituted (x and y=1, 2, 3, 4 or 5), and in which R and R' independently of one another represent identical or different substituents and denote alkyl, cycloalkyl, hydroxyalkyl, aminoalkyl, halogenoalkyl, alkenyl, aryl, aralkyl, ferrocenyl, ferrocenylium, ferrocenylalkyl, acyl, halogenyl, trialkylsilyl, tricycloalkylsilyl, triarylsilyl, triaralkylsilyl or carboxyl, ester, amide or hydrazide groups, or R and R' together form an alkylene bridge with 2 to 4 bridge atoms; a, b, m and n are integers, and m has the value 1 or 2, n has the value 1, 2 or 3 and a×m=b×n; and A is a complexating or very bulky anion which stabilizes the metallicenium cation; and solvates of these salts, for use as medicaments, in particular their use as cytostatics in combating tumors susceptible thereto.

A preferred group of compounds used according to the invention comprises the ferricenium and cobalticenium compounds (M=Fe or Co), which are available inexpensively; for the same reason, unsubstituted compounds (x and y=0) are preferred.

If R or R' is alkyl, hydroxyalkyl, aminoalkyl, halogenoalkyl or halogenyl, x or y preferably has the value 1, 2, 3, 4 or 5. If R or R' is cycloalkyl, alkenyl, aryl, aralkyl, ferrocenyl, ferrocenylium, ferrocenylalkyl, acyl, trialkylsilyl, tricycloalkylsilyl, triarylsilyl or triaralkylsilyl or a carboxyl, ester, amide or hydrazide group, x or y preferably has the value 1 or 2.

"Alkyl" is understood as meaning straight-chain or branched alkyl radicals with 1 to 10, preferably 1 to 6 and in particular 1 to 4, carbon atoms. Specific examples are methyl, ethyl, isopropyl, n-butyl, tert.-butyl, 2-ethylhexyl and n-decyl.

"Cycloalkyl" is understood as meaning cycloaliphatic radicals with 3 to 8, preferably 3 to 6 and in particular 6, carbon atoms. Specific examples are cyclopropyl, cyclobutyl, cyclohexyl, cycloheptyl and cyclooctyl.

"Alkenyl" is understood as meaning unsaturated radicals with 2 to 10, preferably 2 to 6 and in particular 2 to 4, carbon atoms. Vinyl is a specific example.

"Aryl" is understood as meaning aromatic and fused aromatic radicals with 6 to 18, preferably 6 to 14 and in particular 6 to 10, carbon atoms. Phenyl is a specific example.

"Halogen" is understood as meaning fluorine, chlorine, bromine and iodine, fluorine, chlorine and bromine being preferred.

"Acyl" is understood as meaning aliphatic or aromatic acyl radicals with up to 12, preferably up to 7 and in particular up to 4, carbon atoms. Specific examples are acetyl, propionyl and benzoyl.

The hydroxyalkyl, aminoalkyl, halogenoalkyl, alkylene, aralkyl, ferrocenylalkyl, trialkylsilyl, tricycloalkylsilyl, triarylsilyl and triaralkylsilyl substituents are preferably derived from the alkyl, cycloalkyl, aryl or halogen radicals mentioned. The ester groups are preferably alkylester groups with 1 to 4 carbon atoms in the alkyl radical.

Preferred examples of the anion A are anionic complexes of the type $[M'X_4]^{n-}$ (n=1 or 2) or $[M'X_6]^{n-}$ (n=1, 2 or 3), in which M'=B, Bi, Co, Fe, Ga, Hg, Ru o Sb and X=F, Cl, Br or phenyl. Of these, $BF_4^-$, $B\phi_4^-$, $FeCl_4^-$, $FeBr_4^-$, $BiCl_4^-$, $GaCl_4^-$, $PF_6^-$ and $RuCl_4^-$ are particularly preferred.

Other preferred anions A are polyhalides, such as $Br_3$ and $I_3$, vanadates, molybdates, tungstates, oxyvanadates, heteropolyanions, such as molybdophosphates, tungstophosphates and tungstosilicates, Reineckates, hexafluorophosphates, quinonides, quinonedimethanides, $(Cl_3Fe-O-FeCl_3)^{2-}$ and anions of strong organic acids, such as mono-, di- or tri-halogenoacetic acids, cyanoacetic acids, perchloric acid and picric acid.

The metallicenium salts can optionally be solvated, for example by 1, 2 or 3 moles of the free acid corresponding to the anion A.

Representative examples of metallicenium salts which can be used according to the invention are:
1. Ferricenium tetrachloroferrate
2. 1,1'-Bis(triphenylsilyl)ferricenium tetrachloroferrate
3. Ferricenium tetrabromoferrate
4. Ruthenicenium tetrachlororuthenate
5. Ferricenium tetrafluoborate
6. Acetylferricenium tetrafluoborate
7. Biferricenium tetrafluoborate
8. Biferricenium bis(tetrafluoborate)
9. 1'1'''-Diethylbiferricenium bis(tetrafluoborate)
10. Osmocenium tetrafluoborate
11. Ferrocenylmethyl-ferrocenylium tetrafluoborate
12. Ferricenium tetraphenylborate
13. Ferricenium tetrachloroantimonate
14. Ferricenium hexachloroantimonate
15. Ferricenium tetrachlorobismuthate
16. Ferricenium tetrachlorogallate
17. Ferricenium hexafluorophosphate
18. 1,1'-Dimethylferricenium hexafluorophosphate
19. Decamethylferricenium hexafluorophosphate
20. 1,1'-Trimethyleneferricenium hexafluorophosphate
21. Cobalticenium hexafluorophosphate
22. 1,1'-Dimethylcobalticenium hexafluorophosphate
23. Ferricenium 2,3-dichloro-5,6-dicyanohydroquinonide
24. Decamethylferricenium 2,3-dichloro-5,6-dicyanohydroquinonide
25. Cobalticenium 2,3-dichloro-5,6-dicyanohydroquinonide
26. Ferricenium tetracyanoquinodimethanide-tetracyanoquinodimethane
27. 1,1'-Dimethylferricenium tetracyanoquinodimethanide-tetracyanoquinodimethane 28. Cobalticenium tetracyanoquinodimethanide-tetracyanoquinodimethane
29. Ferricenium perchlorate
30. 1,1'-Trimethyleneferricenium perchlorate
31. Cobalticenium perchlorate
32. Ferricenium trichloroacetate-bis(trichloroacetic acid)
33. Ferricenium trichloroacetate-mono(trichloroacetic acid)
34. 1,1'-Dimethylferricenium trichloroacetate-bis(trichloroacetic acid)
35. Biferricenium trichloroacetate-bis(trichloroacetic acid)
36. Ferricenium picrate
37. Ferricenium picrate-picric acid
38. Biferricenium picrate
39. Ferricenium triiodide
40. Hydroxymethylferricenium triiodide
41. Biferricenium triiodide
42. Ferricenium reineckate
43. Ferricenium tungstosilicate
44. Ferricenium oxytrichlorovanadate
45. Ferricenium metatungstate
46. Diferricenium $\mu$-oxo-bis(trichloroferrate)

Most of these compounds are known compounds which can be prepared in accordance with instructions in the literature or by improved processes, which are described in the embodiment examples below. Some metallicenium salts which can be used according to the invention are novel, for example diferricenium $\mu$-oxo-bis(trichloroferrate). The preparation of these novel compounds is also illustrated in the examples.

EXAMPLE 1

Ferricenium tetrachloroferrate can be prepared from ferrocene and iron(III) chloride in a molar ratio of 1:2 in ether by the method described by Nesmeyanov et al., Chem. Ber. Volume 93, page 2729 (1960), but the end product remains contaminated with diferricenium $\mu$-oxo-bis(trichloroferrate) even after several recrystallizations from absolute ethanol. The impurity mentioned manifests itself by infrared absorption at 365 and 316 $cm^{-1}$.

It has now been found that this impurity can be removed quantitatively by recrystallizing the crude tetrachloroferrate once from an acid (pH<0) medium containing chloride ions:

Impure ferricenium tetrachloroferrate is prepared from ferrocene (2 mmol) and anhydrous iron(III) chloride (4 mmol) in ether, with recrystallization from absolute ethanol, by the process of Nesmeyanov et al. The product obtained, the infrared spectrum of which shows that it is a product contaminated with diferricenium $\mu$-oxo-bis(trichloroferrate), can be recrystallized either from freshly distilled thionyl chloride or from 0.15–0.25M aqueous-methanolic (2:98) hydrogen chloride, a ferricenium tetrachloroferrate which is pure according to spectroscopy (disappearance of the maxima at 365 and 316 $cm^{-1}$) and elemental analysis being obtained in the form of blue-black crystal flakes. Found: C, 31.22; H, 2.71; Cl, 36.80. Calculated for $C_{10}H_{10}Cl_4Fe_2$: C, 31.30; H, 2.63; Cl, 36.96. The recrystallization from the acid medium can also be carried out directly with the crude product obtained from ferrocene and iron chloride, by-avoiding the recrystallization from absolute ethanol.

EXAMPLE 2

Although ferricenium trichloroacetate-mono-(trichloroacetic acid) has been described in the literature (Castagnola et al., Journal of Organometallic Chemistry, Volume 60, C17 (1973)), it cannot be reproducibly prepared by the method of these authors from ferrocene and trichloroacetic acid in a molar ratio of 1:3 in benzene solution. Rather, these instructions lead chiefly or completely to the formation of the disolvate: ferricenium trichloroacetate-bis(trichloroacetic acid).

It has now been found that the monosolvate can easily be obtained from the disolvate by hydrolytic detachment of one equivalent of trichloroacetic acid, for example by careful recrystallization from water:

The disolvate required as the starting material is prepared in accordance with the instructions of Hendrickson et al., J. Chem. Phys. Volume 58, page 4666 (1973). A solution of 1.0 g of ferricenium trichloroacetate-bis(trichloroacetic acid) in 9.0 ml of water is kept at the boiling point for 10 to 15 minutes and filtered while still hot. Merely on cooling, dark blue needles crystal separate out, and after the mixture has been left to stand for several hours, these are filtered off, washed with a little ice-water and dried at 60° C./0.2 Torr; melting point: 125°–127° C. A further portion of the salt, melting point: 127°–129° C., can be obtained by highly concentrating the mother liquor (combined with the aqueous wash solutions), briefly warming up the concentrate to dissolve crystals which have already separated out, and leaving the mixture to stand at 50° C. The total yields are 0.4–0.6 g. Found: C, 32.78; H, 2.19; Cl, 41.89. Calculated for $C_{14}H_{11}Cl_6FeO_4$: C, 32.85; H, 2.17; Cl, 41.56. The salt dissolves readily in water and less readily in organic solvents, such as methanol or acetonitrile.

EXAMPLE 3

Although diferricenium $\mu$-oxo-bis(trichloroferrate) is known from the literature (Aharoni and Litt, Journal of Organometallic Chemistry Volume 22, page 179 (1970)), this compound has been erroneously assigned the structure of a ferricenium trichloroferrate by the authors. Moreover, the preparation instructions from these authors have not proved to be reproducible.

It has now been found that the salt can easily be obtained from the ferricenium trichloroferrate described in Example 2 by recrystallization from methanol/acetonitrile to which pyridine has been added, the organic phase serving as a proton-trapping agent:

A solution of 2.0 g of ferricenium tetrachloroferrate obtained according to Example 2 in 15 ml of an $N_2$ saturated mixture of methanol/acetonitrile (1:1) is filtered hot, and a solution of 225 mg of pyridine in 8 ml of ether is then added. The bluish-black crystals of the oxobis(trichloroferrate) which have separated out after the mixture has been left to stand in a closed vessel at −20° C. for several hours are filtered off, washed with ether and dried at 75° C./0.2 Torr. A further portion of the salt is obtained by concentrating the mother liquor to about one third of the original volume in a rotary evaporator and treating the concentrate as above, and a third, impure portion of the salt, obtained from the final liquors, which have been further concentrated, can be obtained in a pure form by recrystallization from the same solvent mixture. Total yield: 0.9–1.1 g. Found: C, b 33.41; H, 2.83; Cl, 30.44; O, 2.35. Calculated for $C_{20}H_{20}Cl_6Fe_4O$: C, 33.71; H, 2.83; Cl, 29.85; O, 2.25. The compound is readily soluble in water and less readily soluble in organic solvents, such as acetonitrile or methanol.

EXAMPLE 4

Although ferricenium picrate-picric acid has been mentioned in the literature (Aly et al., Chem. Commun., 404 (1965)), no preparation instructions have been given.

It has now been found that the salt can be obtained by oxidation of ferrocene in concentrated sulfuric acid and subsequent treatment of the water-diluted ferricenium sulfate solution with picric acid:

A solution of 4.65 g (25 mmol) of ferrocene in 14 ml of concentrated $H_2SO_4$ is left to stand for half an hour and then diluted with 100 ml of ice-water and filtered. A hot solution of 6.87 g (30 mmol) of picric acid in 100 ml of water is added to the filtrate and the mixture is left to stand at room temperature for 24 hours. The crystalline precipitate formed is filtered off, washed with a little water and ether and dried at 50° C./0.2 Torr. 5.1 g of crude product are obtained as green-black crystals, which are carefully recrystallized, without prolonged heating, from ethanol, ferricenium picrate-picric acid being obtained in the form of blackish needles, melting point: 128°–130° C. Found: C, 41.99; H, 2.40; N, 12.30. Calculated for $C_{22}H_{15}FeN_6O_{14}$: C, 41.08; H, 2.35; N, 13.06. The salt is readily soluble in water and less readily soluble in organic solvents, such as alcohols or acetonitrile.

The matallicenium salts according to the invention exhibit a cytostatic action in animal experiments. This is tested as follows:

Female $CF_1$ mice are each given about $6 \times 10^6$ Ehrlich ascites tumor cells by means of intraperitoneal injection and, 24 hours later, a single intraperitoneal dose of substance (dose range of 20 to 500 mg/kg) in physiological saline solution (0.4 ml). In each case 5 to 10 animals are tested per dose. If appropriate, the preparation can be buffered to a pH of 4 to 7, for example with sodium bicarbonate or tris-(hydroxymethyl)-aminomethane, in order to avoid local irritation at the injection site. A group of untreated control animals which were injected intraperitoneally with 0.4 ml of physiological saline solution without administration of the substance is also run for each experimental series.

The tumor development in the individual dose ranges is evaluated with the aid of the weight course and survival time. The dose-dependent number of tumor fatalities, toxicity fatalities and surviving, cured animals and the associated percentage increase in the average survival time are determined for each substance.

The results obtained by testing ferricenium trichloroacetate-mono(trichloroacetic acid), ferricenium trichloroacetate-bis(trichloroacetic acid), ferricenium picrate and diferricenium-oxo-bis(trichloroferrate) are reproduced in the following Tables I to IV.

TABLE I

Effect of $Cp_2Fe^+CCl_3COO^-.CCl_3COOH$ (*) on the survival time of mice carrying Ehrlich tumors

| Dose [mg/kg] | Number of experimental animals | Surviving animals (a) Number | Surviving animals (a) Proportion [%] | Average survival time (a) [d] | Increase in the average survival time (a) (b) [%] |
|---|---|---|---|---|---|
| 20 | 6 | 1 | 17 | 27.3 | +72.8 |
| 40 | 6 | 1 | 17 | 28.3 | +79.1 |
| 60 | 6 | 3 | 50 | 50.3 | +218.4 |
| 80 | 6 | 4 | 67 | 64.0 | +305.1 |
| 100 | 6 | 3 | 50 | 58.3 | +269.0 |
| 120 | 6 | 5 | 83 | 76.8 | +386.1 |
| 140 | 6 | 5 | 83 | 76.4 | +383.5 |
| 160 | 6 | 5 | 83 | 75.7 | +379.1 |
| 180 | 6 | 4 | 67 | 61.3 | +288.0 |
| 200 | 6 | 4 | 67 | 61.0 | +286.1 |
| 220 | 6 | 2 | 33 | 32.5 | +105.7 |
| 240 | 6 | 1 | 17 | 17.8 | +12.7 |
| 260 | 6 | 0 | 0 | 3.3 | −79.1 |

(a) Up until the deadline (90th day after transplantation)
(b) Based on the untreated control animals (average survival time 15.8 days)
(*) Cp = cyclopentadienyl $C_5H_5$

TABLE II

Effect of $Cp_2Fe^+CCl_3COO^-.2CCl_3COOH$(*) on the survival time of mice carrying Ehrlich ascites tumors

| Dose [mg/kg] | Number of experimental animals | Surviving animals (a) Number | Surviving animals (a) Proportion [%] | Average survival time (a) [d] | Increase in the average survival time (a) (b) [%] |
|---|---|---|---|---|---|
| 20 | 6 | 0 | 0 | 15.5 | +1.3 |
| 40 | 6 | 0 | 0 | 15.3 | ±0.0 |
| 60 | 6 | 0 | 0 | 15.8 | +3.3 |
| 80 | 6 | 0 | 0 | 16.2 | +5.9 |
| 100 | 6 | 1 | 17 | 25.3 | +65.4 |
| 120 | 6 | 2 | 33 | 38.5 | +151.6 |
| 140 | 6 | 2 | 33 | 38.7 | +152.9 |
| 160 | 6 | 4 | 67 | 65.0 | +324.8 |
| 180 | 6 | 4 | 67 | 66.3 | +333.3 |
| 200 | 6 | 5 | 83 | 78.0 | +409.8 |

TABLE II-continued

Effect of $Cp_2Fe^+CCl_3COO^-.2CCl_3COOH$(*) on the survival time of mice carrying Ehrlich ascites tumors

| Dose [mg/kg] | Number of experimental animals | Surviving animals (a) Number | Surviving animals (a) Proportion [%] | Average survival time (a) [d] | Increase in the average survival time (a) (b) [%] |
|---|---|---|---|---|---|
| 220 | 6 | 6 | 100 | 90.0 | +488.2 |
| 240 | 6 | 6 | 100 | 90.0 | +488.2 |
| 260 | 6 | 6 | 100 | 90.0 | +488.2 |
| 280 | 6 | 6 | 100 | 90.0 | +488.2 |
| 300 | 6 | 6 | 100 | 90.0 | +488.2 |
| 320 | 6 | 5 | 83 | 76.0 | +396.7 |
| 340 | 6 | 6 | 100 | 90.0 | +488.2 |
| 360 | 6 | 4 | 67 | 61.8 | +300.0 |
| 380 | 6 | 3 | 50 | 47.0 | +207.2 |
| 400 | 6 | 4 | 67 | 61.2 | +303.9 |
| 420 | 6 | 2 | 33 | 33.0 | +115.7 |
| 440 | 6 | 1 | 17 | 18.3 | +19.6 |
| 460 | 6 | 2 | 33 | 32.5 | +112.4 |
| 480 | 6 | 0 | 0 | 3.5 | −77.1 |
| 500 | 6 | 0 | 0 | 3.2 | −79.1 |

(a) Up until the deadline (90th day after transplantation)
(b) Based on the untreated control animals (average survival time 15.3 days)
(*) Cp = cyclopentadienyl $C_5H_5$

TABLE III

Effect of $Cp_2Fe^+C_6H_2N_3O_7$(*) on the survival time of mice carrying Ehrlich ascites tumors

| Dose [mg/kg] | Number of experimental animals | Surviving animals (a) Number | Surviving animals (a) Proportion [%] | Average survival time (a) [d] | Increase in the average survival time (a) (b) [%] |
|---|---|---|---|---|---|
| 20 | 6 | 0 | 0 | 14.2 | −2.7 |
| 40 | 6 | 0 | 0 | 14.5 | −0.7 |
| 60 | 6 | 0 | 0 | 14.5 | −0.7 |
| 80 | 6 | 0 | 0 | 15.7 | +7.5 |
| 100 | 6 | 1 | 17 | 28.3 | +93.8 |
| 120 | 6 | 1 | 17 | 28.0 | +91.8 |
| 140 | 6 | 3 | 50 | 52.5 | +259.6 |
| 160 | 6 | 2 | 33 | 40.3 | +176.0 |
| 180 | 6 | 3 | 50 | 50.0 | +242.5 |
| 200 | 6 | 5 | 83 | 78.0 | +434.2 |
| 220 | 6 | 6 | 100 | 90.0 | +516.4 |
| 240 | 6 | 6 | 100 | 90.0 | +516.4 |
| 260 | 6 | 5 | 83 | 75.5 | +417.1 |
| 280 | 6 | 6 | 100 | 90.0 | +516.4 |
| 300 | 6 | 3 | 50 | 48.7 | +233.6 |
| 320 | 6 | 4 | 67 | 62.0 | +324.7 |
| 340 | 6 | 2 | 33 | 35.2 | +141.1 |
| 360 | 6 | 3 | 50 | 48.0 | +228.8 |
| 380 | 6 | 1 | 17 | 19.0 | +30.1 |
| 400 | 6 | 2 | 33 | 34.0 | +132.9 |
| 420 | 6 | 0 | 0 | 4.5 | −69.2 |

(a) Up until the deadline (90th day after transplantation)
(b) Based on the untreated control animals (average survival time 14.6 days)
(*) Cp = cyclopentadienyl $C_5H_5$; $C_6H_2N_3)_7{}^-$ = picrate

TABLE IV

Effect of $(Cp_2Fe^+)_2(Cl_3Fe-O-FeCl_3)^{2-}$(*) on survival time of mice carrying Ehrlich ascites tumors

| Dose [mg/kg] | Number of experimental animals | Surviving animals (a) Number | Surviving animals (a) Proportion [%] | Average survival time (a) [d] | Increase in the average survival time (a) (b) [%] |
|---|---|---|---|---|---|
| 20 | 6 | 1 | 17 | 28.7 | +78.3 |
| 40 | 6 | 2 | 33 | 40.0 | +148.4 |
| 60 | 6 | 1 | 17 | 27.8 | +72.7 |
| 80 | 6 | 3 | 50 | 52.8 | +228.0 |
| 100 | 6 | 2 | 33 | 40.7 | +152.8 |
| 120 | 6 | 3 | 50 | 53.3 | +231.1 |
| 140 | 6 | 4 | 67 | 65.0 | +303.7 |
| 160 | 6 | 4 | 67 | 63.8 | +296.3 |
| 180 | 6 | 5 | 83 | 77.7 | +382.5 |

TABLE IV-continued

Effect of $(Cp_2Fe^+)_2 (Cl_3Fe\text{—}O\text{—}FeCl_3)^{2-}$ (*) on survival time of mice carrying Ehrlich ascites tumors

| Dose [mg/kg] | Number of experimental animals | Surviving animals (a) | | Average survival time (a) [d] | Increase in the average survival time (a) (b) [%] |
|---|---|---|---|---|---|
| | | Number | Proportion [%] | | |
| 200 | 6 | 4 | 67 | 62.2 | +286.3 |
| 220 | 6 | 4 | 67 | 63.5 | +294.4 |
| 240 | 6 | 4 | 67 | 63.7 | +295.7 |
| 260 | 6 | 3 | 50 | 48.2 | +199.4 |
| 280 | 6 | 3 | 50 | 48.2 | +199.4 |
| 300 | 6 | 1 | 17 | 18.3 | +13.7 |

(a) Up until the deadline (90th day after transplantation)
(b) Based on the untreated control animals (average survival time 16.1 days)
(*) Cp = cyclopentadienyl $C_5H_5$ For combating tumors susceptible thereto, the metallicenium salts according to the invention can be employed as such or as medicaments containing at least one metallicenium salt of the general formula I, in addition to pharmaceutically acceptable excipients, diluents and/or auxiliaries. The pharmaceutical formulations of the active compounds are preferably in the form of unit doses matched to the particular mode of administration. A unit dose can be, for example, a tablet, a capsule, a suppository or a measured volume of a powder, granules or a solution or suspension. "Unit dose" is understood as meaning a physically specific unit containing an individual amount of the active compound mixed with a suitable pharmaceutical excipient, diluent and/or auxiliary. The amount of active compound is chosen here so that one or more units are usually sufficient for an individual therapeutic administration. The unit dose can also be divisible, for example in the form of grooved tablets, if only a fraction, for example one half or one quarter, of the divisible unit is required for an individual therapeutic administration. The medicaments of the invention contain, if they are in the form of a unit dose, 1 to 10,000 mg, preferably 5 to 7,500 mg, of active compound.

The medicaments of the invention are preferably used orally, rectally or parenterally, for example intravenously, subcutaneously, intramuscularly, intrapleurally, intraperitoneally, intrafocally or perifocally. The therapeutic administration can be effected continuously by means of infusion over several hours or by one to several individual administrations or individual injections. The administration sequence and the dose administered can vary greatly as a function of the nature and stage of the disease and depending on the treatment regime, in particular on the number and dosage level of combination products administered. For example, initial treatment can be performed with 200 to 800 mg i.v. daily or with individual doses, for example 10 to 40 mg/kg i.v., at corresponding intervals, and subsequent long-term treatment can be carried out with 1 to 4 tablets, each of 50 mg of active compound.

The medicaments as a rule consist of the active compounds according to the invention and non-toxic, pharmaceutically acceptable medicament excipients, which are used as an admixture in solid, semi-solid or liquid form or as a coating agent, for example in the form of a capsule, a tablet coating, a sachet or another container for the active compound. The excipient can serve here, for example, as an agent for promoting absorption of the medicament by the body or as a formulation auxiliary, sweetener, flavoring agent, colorant or preservative.

Tablets, coated tablets, hard and soft gelatin capsules, dispersible powders, granules, aqueous and oily suspensions, emulsions, solutions and syrups, for example, are suitable for oral administration.

Tablets can contain inert diluents, such as calcium carbonate, calcium phosphate, sodium phosphate or lactose; granulating and distributing agents, such as starch, gelatin or gum acacia; and lubricants, such as aluminum stearate, magnesium stearate, talc or silicone oil. If appropriate, the tablets can be provided with a coating, which can also be such that it effects delayed dissolution and absorption of the medicament in the gastrointestinal tract and thus, for example, a better tolerance or longer period of action.

Gelatin capsules can contain the active compound mixed with a solid diluent (for example calcium carbonate or kaolin) or an oily diluent (for example olive oil, arachis oil or paraffin oil).

Examples of suitable suspending agents are sodium carboxymethylcellulose, methylcellulose, hydroxypropylcellulose, sodium alginate, polyvinylpyrrolidone, gum tragacanth or gum acacia; examples of suitable dispersing agents and wetting agents are polyoxyethylene stearate, heptadecaethyleneoxycetanol, polyoxyethylenesorbitol monooleate, polyoxyethylenesorbitan monooleate and lecithin; examples of suitable preservatives are methyl and propyl hydroxybenzoate; and examples of flavoring agents and sweeteners are sucrose, lactose, dextrose and invert sugar syrup.

Oily suspensions can contain, for example, arachis, olive, sesame, coconut or paraffin oil and thickeners, such as beeswax, hard paraffin or cetyl alcohol, sweeteners, flavoring agents and/or antioxidants.

Water-dispersible powders and granules contain the active compound mixed with dispersing agents, wetting agents and suspending agents, for example the above-mentioned substances and/or dimethyl sulfoxide, and with sweeteners, flavoring agents and/or colorants.

Emulsions can contain, for example, olive, arachis or paraffin oil, in addition to emulsifiers, such as gum acacia, gum tragacanth, phosphatides, sorbitan monooleate or polyoxyethylenesorbitan monooleate, sweeteners and/or flavoring agents.

Suppositories which are prepared with the aid of binders which melt at rectal temperature, for example cocoa butter or polyethylene glycols, are suitable for rectal use.

The medicaments can be administered parenterally as sterile isotonic saline solutions or other solutions. A solubilizing agent, such as dimethyl sulfoxide, may be added in order to achieve a uniform solution or suspension, but this is usually not necessary.

In all the presentation forms, the medicaments of the invention can also contain buffer substances, for example sodium bicarbonate or tris(hydroxymethyl-)aminomethane.

Besides the metallicenium salts according to the invention, the medicaments can contain one or more other pharmacologically active constituents from other groups of medicaments which have a cytostatic action, for example alkylating agents, antimetabolites and cytostatic alkaloids, antibiotics, enzymes and heavy metal compounds. The medicaments can furthermore optionally contain immunosuppressant substances and vitamins. The additional substances mentioned can also be added to the active compounds according to the invention in separate pharmaceutical formulations as combination products.

The active compound content of the medicaments is usually 0.01 to 95% by weight, preferably 0.1 to 85% by weight, based on the finished medicament.

We claim:

1. A pharmaceutical composition containing a cytostatically active amount of at least one metallicenium salt of the general formula I

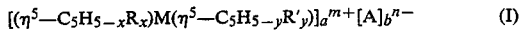

$$[(\eta^5-C_5H_{5-x}R_x)M(\eta^5-C_5H_{5-y}R'_y)]_a{}^{m+}[A]_b{}^{n-} \quad (I)$$

in which m is Fe, Co, Ni, Ru or Os; $C_5H_{5-x}R_x$ and $C_5H_{5-y}R'_y$ denote cyclopendadienyl rings which, independently of one another, can be unsubstituted (x and y=0) or mono-, di-, tri-, tetra- or penta-substituted (x and y=1, 2, 3, 4 or 5), and in which R and R' independently of one another represent identical or different substituents and denote alkyl, cycloalkyl, hydroxyalkyl, aminoalkyl, halogenoalkyl, alkenyl, aryl, aralkyl, ferrocenyl, ferrocenylium, ferrocenylalkyl, acyl, halogenyl, trialkylsilyl, tricycloalkylsilyl, triarylsilyl, triaralkylsilyl or carboxyl, ester, amide or hydrazide groups, or R and R' together form an alkylene bridge with 2 to 4 bridge atoms; a, b, m and n are integers, and m has the value 1 or 2, n has the value 1, 2 or 3 and a×m=b×n; and A is a complexating or very bulky anion which stabilizes the metallicenium cation; or a solvate of these salts and a pharmaceutically acceptable excipient, diluent or auxillary agent.

2. The pharmaceutical composition as claimed in claim 1, in which m is Fe or Co.

3. The pharmaceutical composition as claimed in claim 1, in which x and y=0.

4. The pharmaceutical composition as claimed in claim 1, in which $[A]n^-$ is $BF_4^-$, $B\phi_4^-FeCl_4^-$, $FeBr_4^-$, $BiCl_4^-$, $GaCl_4^-$, $PF_6^-$, $RuCl_4^-$ or $(Cl_3Fe-O-FeCl_3)^{2-}$.

5. The pharmaceutical composition as claimed in claim 1, in which A is a quinonide or quinonedimethanide, a polyhalide, vanadate, oxyvanadate, molybdate, tungstate, heteropolyanion or reineckate or the anion of a strong organic acid.

6. The pharmaceutical composition as claimed in claim 5, in which A is an anion of a strong organic acid chosen from the group consisting of mono-, di- and tri-halogenoacetates, cyanoacetate and picrate and the metallicenium salt is optionally solvated with the free acid.

7. The pharmaceutical composition as claimed in claim 1, which contains at least one compound chosen from the group consisting of ferricenium trichloroacetate-mono- and -bis-(trichloroacetic acid); diferricenium μ-oxo-bis(trichloroferrate); ferricenium picrate and ferricenium picrate-picric acid.

8. A method of combatting tumors by administering to a patient in need thereof an anti-tumor effective amount of a metallicenium salt of the general formula I

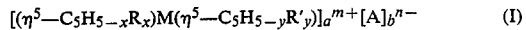

$$[(\eta^5-C_5H_{5-x}R_x)M(\eta^5-C_5H_{5-y}R'_y)]_a{}^{m+}[A]_b{}^{n-} \quad (I)$$

in which m is Fe, Co, Ni, Ru or Os; $C_5H_{5-x}R_x$ and $C_5H_{5-y}R'_y$ denote cyclopendadienyl rings which, independently of one another, can be unsubstituted (x and y=0) or mono-, di-, tri-, tetra- or penta-substituted (x and y=1, 2, 3, 4 or 5), and in which R and R' independently of one another represent identical or different substituents and denote alkyl, cycloalkyl, hydroxyalkyl, aminoalkyl, halogenoalkyl, alkenyl, aryl, aralkyl, ferrocenyl, ferrocenylium, ferrocenylalkyl, acyl, halogenyl, trialkylsilyl, tricycloalkylsilyl, triarylsilyl, triaralkylsilyl or carboxyl, ester, amide or hydrazide groups, or R and R' together form an alkylene bridge with 2 to 4 bridge atoms; a, b, m and n are integers, and m has the value 1 or 2, n has the value 1, 2 or 3 and a×m=b×n; and A is a complexating or very bulky anion which stabilizes the metallicenium cation; or a solvate of these salts, said patient having a tumor susceptible to said metallicenium salt.

9. The method as claimed in claim 8, wherein M is Fe or Co.

10. The method as claimed in claim 8, wherein x and y=0.

11. The method as claimed in claim 8, wherein $[A]^{n-}$ is $BF_4^-$, $B\phi_4^-$, $FeCl_4^-$, $FeBr_4^-$, $BiCl_4^-$, $GaCl_4^-$, $PF_6^-$, $RuCl_4^-$ or $(Cl_3Fe-O-FeCl_3)^{2-}$.

12. The method as claimed in claim 8, wherein A denotes a quinonide or quinonedimethanide, a polyhalide, vanadate, oxyvanadate, molybdate, tungstate, heteropolyanion or Reineckate or the anion of a strong organic acid.

13. The method as claimed in claim 12, wherein A is an anion of a strong organic acid chosen from the group consisting of mono-, di- or tri-halogenoacetates, cyanoacetate or picrate and the metalliceneium salt is optionally solvated with free acid.

14. The method as claimed in claim 8, wherein at least one compound chosen from the group consisting of ferricenium trichloroacetate-mono- and -bis-(trichloroacetic acid); diferricenium u-oxo-bis(trichloroferrate); ferricenium picrate and ferricenium picrate-picric acid is used.

* * * * *